(12) United States Patent
Reilly

(10) Patent No.: US 8,062,263 B2
(45) Date of Patent: Nov. 22, 2011

(54) SUPPORT SYSTEM FOR A FEEDING TUBE

(76) Inventor: William Reilly, Branson, MO (US)

( * ) Notice: Subject to any disclaimer, the term of this patent is extended or adjusted under 35 U.S.C. 154(b) by 457 days.

(21) Appl. No.: 11/969,563

(22) Filed: Jan. 4, 2008

(65) Prior Publication Data

US 2009/0177164 A1   Jul. 9, 2009

(51) Int. Cl.
*A61M 5/32* (2006.01)
(52) U.S. Cl. ...................................................... 604/179
(58) Field of Classification Search .................. 604/174, 604/179, 177
See application file for complete search history.

(56) References Cited

U.S. PATENT DOCUMENTS 5,403,285 A * 4/1995 Roberts .......................... 604/179
5,685,859 A * 11/1997 Kornerup ....................... 604/180

* cited by examiner

*Primary Examiner* — Theodore Stigell
*Assistant Examiner* — Bradley Osinski
(74) *Attorney, Agent, or Firm* — Michael Ries

(57) ABSTRACT

A support system for supporting a feeding tube of a person is disclosed. The support system comprises an elongated flexible band, a disc and a sling mechanism. The elongated flexible band is adapted to circumscribe the person's body, at least partially covering abdomen region of the person. The disc is disposed on the elongated flexible band and is capable of securing the feeding tube. The sling mechanism is functionally coupled to the elongated flexible band and provides support to the feeding tube, for example, while the tube is not being used to feed a user.

11 Claims, 3 Drawing Sheets

SUPPORT SYSTEM FOR A FEEDING TUBE

FIELD OF THE INVENTION

The present invention relates generally to medical appliances, and, more particularly, to a support system for supporting a gastronomy feeding tube that is partially implanted in the body of a patient.

BACKGROUND OF THE INVENTION

A gastronomy feeding tube finds application for people facing health difficulties such as intestinal infections or other eating or feeding disorders. Such a feeding tube implanted in the body of a patient, is an alternate solution for oral intake of food, and is used for supplying nourishment to the body of the patient directly through the feeding tube. More specifically, food is directly fed by means of the feeding tube into the intestines, usually by gravity or through a vial inserted in one end of the feeding tube. When feeding is necessary the feeding tube is then positioned to receive the feeding mechanism which is connected to the feeding tube to supply food into the stomach of the patient.

Presently, existing support systems for feeding tubes have numerous limitations. For example, theses support systems are not able to shelter and retain the feeding tube adequately. The inadequate support of the feeding tube may cause pulling on the loose end of the feeding tube consciously or unconsciously. This may result into withdrawal of the feeding tube from its point of insertion in abdominal wall of a patient. The withdrawal of the feeding tube from the point of insertion in the abdominal wall is painful and may require immediate medical and surgical attention for reinsertion of the feeding tube. Further, most of the existing support systems include holding disks for supporting the feeding tubes that are stitched to the skin of the patients. Accordingly, there arises a problem in cleaning the underneath portion of the holding disks. Therefore, the existing support systems may experience problems in cleaning and disinfection of the feeding tube.

Further, the existing support systems do not have any mechanism to support the feeding tube while the tube is not in use. This may result in discomfort and increases the risk of the nourishment falling out of the feeding tube.

Accordingly, what is needed is a support system that can retain and shelter the feeding tube securely, and in turn, avoiding the withdrawal of the feeding tube from the abdominal wall of the patient. Further, the support system should facilitate the cleaning of the feeding tube in order to prevent odor and facilitate keeping the feeding tube disinfected.

SUMMARY OF THE INVENTION

In view of the foregoing disadvantages inherent in the prior art, the general purpose of the present invention is to provide a support system configured to include all the advantages of the prior art, and to overcome the drawbacks inherent therein.

Therefore, an object of the present invention is to provide a support system for a feeding tube of a person and is adjustable for individuals of different abdominal sizes.

Another object of the present invention is to provide a support system that may be easily detachable from the person's body.

Yet another object of the present invention is to provide a support system with an elongated flexible band that may be cleaned and disinfected, and is reusable.

It is yet another object of the present invention is to provide a support system which has an elongated flexible band capable of being used on both sides of elongated flexible band.

Therefore, in one aspect, the present invention provides a support system for supporting a feeding tube of a person. The support system comprises an elongated flexible band, cooperative fasteners, a disc, and a sling mechanism.

The elongated flexible band is adapted to circumscribe the person's body, which at least partially covers abdomen region of the person. The cooperative fasteners are disposed at opposite ends of the elongated flexible band along a length of the elongated flexible band. The cooperative fasteners are configured to detachably secure the opposite ends of the elongated flexible band to circumscribe the person's body. The disc is disposed at the elongated flexible band and is capable of securing the feeding tube.

Further, the sling mechanism is capable of supporting the feeding tube, for example, while the feeding tube is not in use. The sling mechanism comprises a first structural element and a second structural element. The first structural element is capable of securing a portion of the feeding tube, for example, while the tube is not in use. Each of the first structural element and the second structural element has a first end and a second end. The first end of the first structural element is connected to the disc and the first end of the second structural element is connected to the elongated flexible band. The second end of the second structural element is capable of securing the second end of the first structural element.

In another aspect, the present invention provides a support system for supporting a feeding tube of a person. The support system comprises an elongated flexible band, cooperative fasteners, a disc, and a sling mechanism.

The elongated flexible band is adapted to circumscribe the person's body, which at least partially covers abdomen region of the person. The cooperative fasteners are disposed at opposite ends of the elongated flexible band along the length of the elongated flexible band. The cooperative fasteners are configured to detachably secure the opposite ends of the elongated flexible band to circumscribe the person's body. The disc is detachably disposed at the elongated flexible band and is capable of securing the feeding tube.

Further, the sling mechanism is capable of supporting the feeding tube, for example, while the tube is not in use. The sling mechanism comprises a first structural element and a second structural element. The first structural element capable of securing a portion of the feeding tube. Each of the first structural element and the second structural element has a first end and a second end. The first end of the first structural element is connected to the disc and the first end of the second structural element is connected to the elongated flexible band. The second end of the second structural element is capable of securing the second end of the first structural element.

These together with other aspects of the present invention, along with the various features of novelty that characterize the present invention, are pointed out with particularity in the claims annexed hereto and form a part of this present invention. For a better understanding of the present invention, its operating advantages, and the specific objects attained by its uses, reference should be made to the accompanying drawings and descriptive matter in which there are illustrated exemplary embodiments of the present invention.

BRIEF DESCRIPTION OF THE DRAWINGS

The advantages and features of the present invention will become better understood with reference to the following detailed description and claims taken in conjunction with the accompanying drawings, wherein like elements are identified with like symbols, and in which:

Like reference numerals refer to like parts throughout the description of several views of the drawings.

DETAILED DESCRIPTION OF THE INVENTION

The exemplary embodiments described herein detail for illustrative purposes are subject to many variations in structure and design. It should be emphasized, however, that the present invention is not limited to a particular support system, as shown and described. It is understood that various omissions and substitutions of equivalents are contemplated as circumstances may suggest or render expedient, but these are intended to cover the application or implementation without departing from the spirit or scope of the claims of the present invention.

The terms "first," "second," and the like, herein do not denote any order, quantity, or importance, but rather are used to distinguish one element from another, and the terms "a" and "an" herein do not denote a limitation of quantity, but rather denote the presence of at least one of the referenced item.

Figure 1:
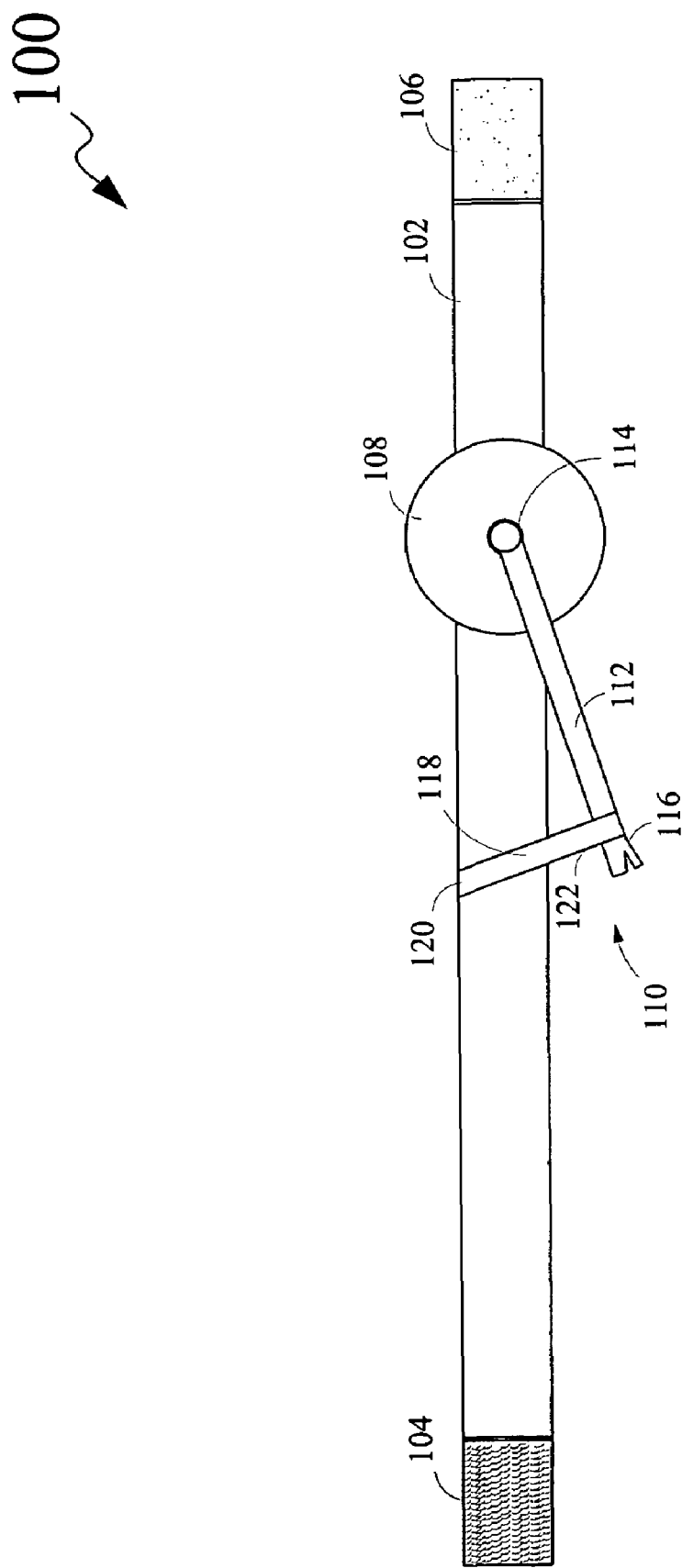
FIG. 1 is a top view of a support system, according to an exemplary embodiment of the present invention.
Figure 2:
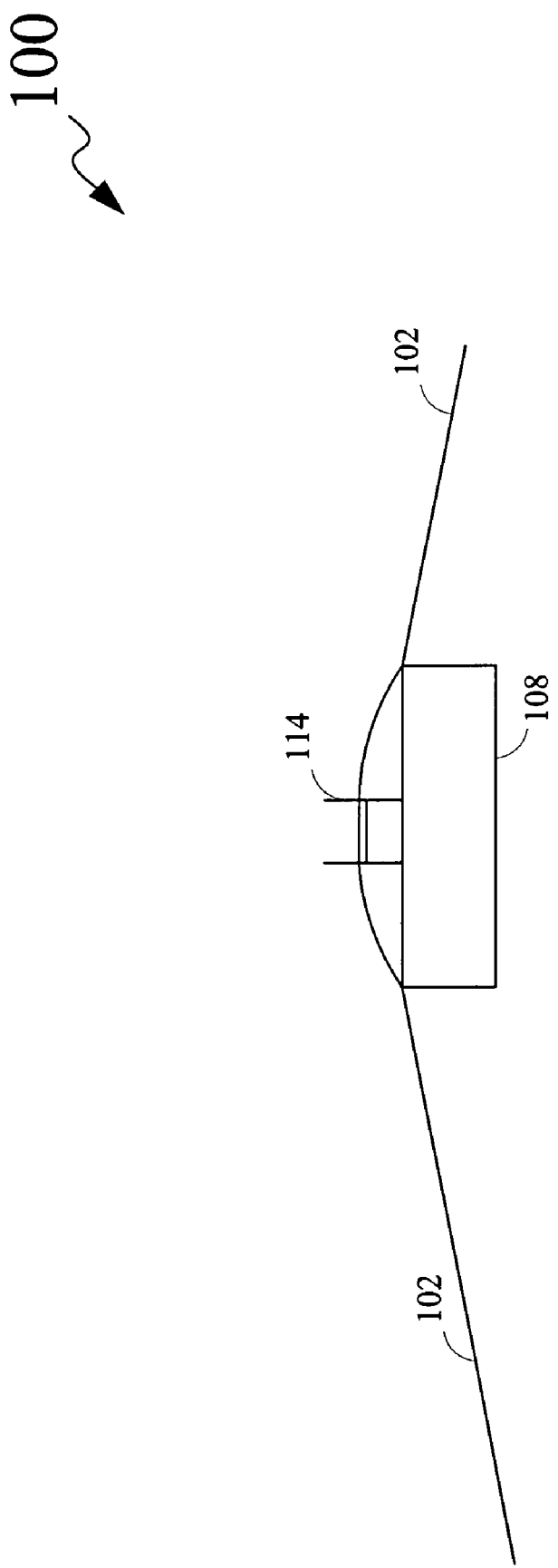
FIG. 2 is a front view of the support system, according to an exemplary embodiment of the present invention.

Referring to FIGS. 1 and 2, a support system 100 for supporting a feeding tube is shown. FIG. 1 is a top view of the support system 100 and FIG. 2 is a front view of the support system 100, according to an exemplary embodiment of the present invention. The support system 100 comprises an elongated flexible band 102, cooperative fasteners 104 and 106, a disc 108, and a sling mechanism 110.

The elongated flexible band 102 is configured such that it may circumscribe a person's body by at least partially covering abdomen region of the person. The elongated flexible band 102 may be of varying adjustable length such that the same elongated flexible band 102 may be utilized for different individuals with different abdominal sizes. Accordingly, in an embodiment of the present invention, a length of the elongated flexible band 102 may be adjustable in the range of 34 inches to 46 inches of abdominal size. However, the elongated flexible band 102 for the size range of 40 inches to 46 inches may be wider as compared to the elongated flexible band 102 for the size range of 34 inches to 40 inches. The elongated flexible band 102 is capable of being used by both sides.

As shown in FIG. 1, the cooperative fasteners 104 and 106 are disposed at opposite ends along the length of the elongated flexible band 102. The cooperative fasteners 104 and 106 are configured to detachably secure the opposite ends of the elongated flexible band 102 around the person's body. More specifically, the cooperative fasteners 104 and 106 are configured as mating fasteners to each other such that the cooperative fasteners 104 and 106 may be affixed when held together and also gets separated when pulled apart. In one embodiment, the cooperative fasteners 104 and 106 may be Velcro cooperative fasteners. For example, as shown in FIG. 1, the cooperative fastener 104 may be a Velcro fastener and the cooperative fastener 106 may be a Velcro back fastener. In another embodiment, the cooperative fasteners 104 and 106 can be mating hooks, mating clips or eyelets.

As shown in FIGS. 1 and 2, in one embodiment of the present invention, the disc 108 is disposed at a central portion of the elongated flexible band 102. However, it will be apparent to a person skilled in the art that the disc 108 may be disposed at any convenient position of the elongated flexible band 102 depending upon the location of a feeding tube (not shown) in the person's body. The disc 108 is capable of securing the feeding tube. More specifically, the disc 108 is capable of sheltering and retaining the feeding tube when the feeding tube is not engaged for the feeding procedure. The feeding tube is retained in the disc 108 until a subsequent feeding procedure is to be accomplished. The disc 108 is configured in a manner such that it may be flipped conveniently to facilitate cleaning of the feeding tube, which in turn, helps in eliminating any possibility of irritation, infection or odor. During the feeding operation, the present invention provides the sling mechanism 110 to provide the support to the feeding tube.

The sling mechanism 110 is capable of supporting the feeding tube, for example, while the tube is not being used to feed a user. The sling mechanism 110 comprises a first structural element 112 and a second structural element 118. The first structural element 112 comprises a first end 114 and a second end 116 and is capable of securing a portion of the feeding tube during the feeding operation. The second structural element 118 has a first end 120 and a second end 122. The first end 114 of the first structural element 112 is connected to the disc 108 and the first end 120 of the second structural element 118 is connected to the elongated flexible band 102. The second end 122 of the second structural element 118 is capable of supporting the second end 116 of the first structural element 112.

During the feeding operation, in an embodiment of the present invention, the portion of the feeding tube, which is outside of the disc 108, may be positioned over the first structural element 112. In another embodiment of the present invention, the first structural element 112 may be of a tubular structure and the portion of the feeding tube may be received within the first structural element 112. Further, the second structural element 118 provides support to the first structural element 112, which in turn, provides support to the feeding tube during the feeding operation. The first structural element 112 and the second structural element 118 may have a locking mechanism (not shown) at the second ends 116 and 122 respectively, such that the second structural element 118 is capable of supporting the first structural element 112.

Figure 3:
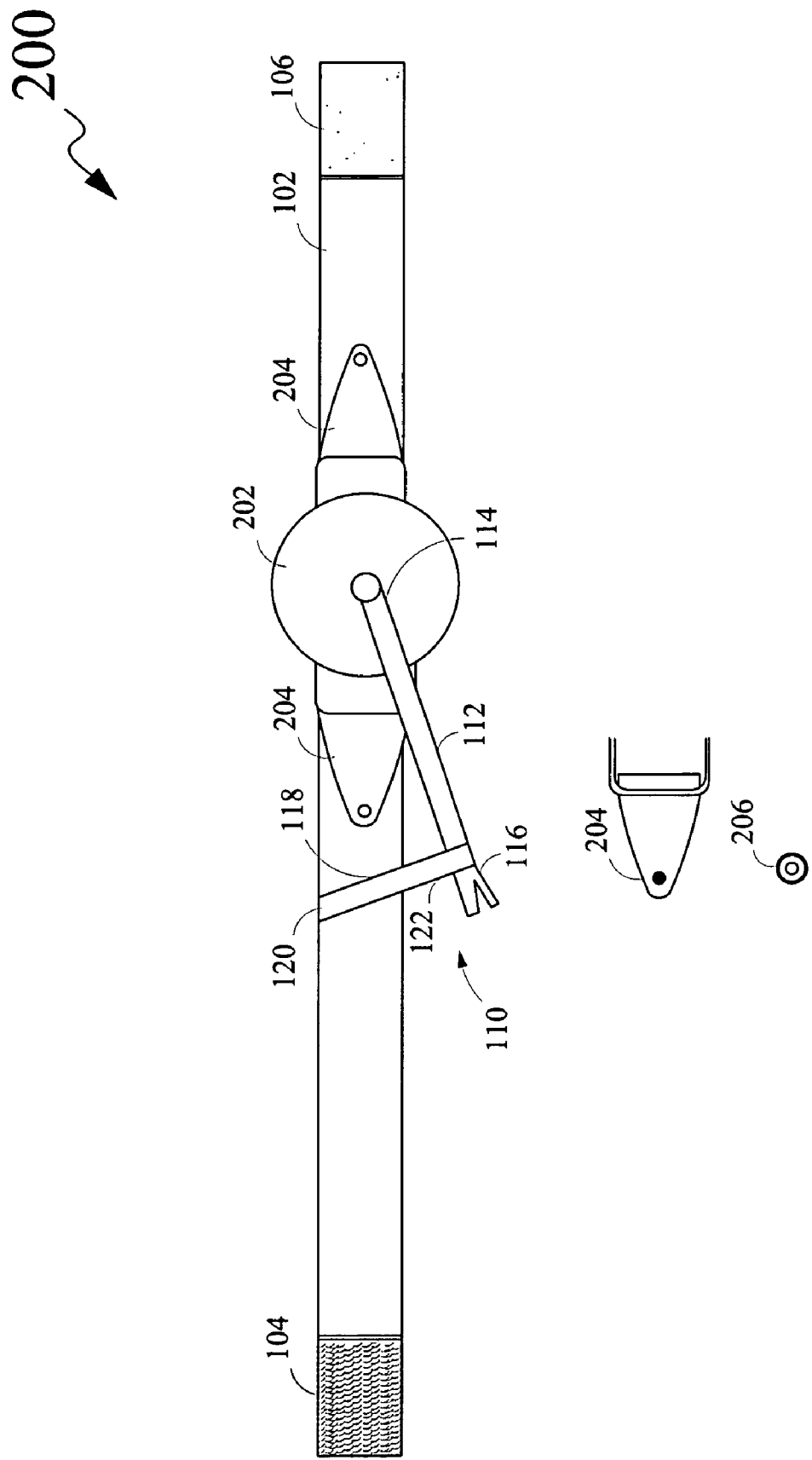
FIG. 3 is a top view of a support system with snap fasteners, according to another exemplary embodiment of present the invention.

Referring now to FIG. 3, a support system 200 is shown, according to another exemplary embodiment of the present invention. The support system 200 includes the elongated flexible band 102, the cooperative fasteners 104 and 106, a disc 202, and the sling mechanism 110 including the first structural element 112 and the second structural element 118. The same reference numerals have been used in FIG. 3 corresponding to same components as referred to in FIGS. 1, 2. Accordingly, the corresponding components have not been described with respect to FIG. 3. In this embodiment, the disc 202 is disposed on the elongated flexible band 102 such that the disc 202 may be detached from the elongated flexible band 102. Accordingly, in one embodiment of the present invention, the disc 202 comprises a pair of snap fasteners 204 (hereinafter referred to as 'snap fasteners 204'). The snap fasteners 204 are capable of detachably securing the elongated flexible band 102 to the disc 202.

In an embodiment of the present invention, the snap fasteners 204, which are male fasteners, may be engaged to snap fasteners 206, which are female fasteners on the elongated flexible band 102. However, it will be apparent to a person skilled in the art that the snap fasteners 204 and the snap fasteners 206 may be configured interchangeably as male and female fasteners. Further, in another embodiment of the present invention, the snap fasteners 204 may be Velcro fasteners. This embodiment of the present invention helps in cleaning of the feeding tube by facilitating the detachment of the elongated flexible band 102 from the disc 202.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, and to thereby enable others skilled in the art to best utilize the invention and various embodiments with various modifications as are suited to the particular use contemplated. It is understood that various omissions and substitutions of equivalents are contemplated as circumstances may suggest or render expedient, but such omissions and substitutions are intended to cover the application or implementation without departing from the spirit or scope of the claims of the present invention.

What is claimed is:

1. A support system for a feeding tube, comprising:
an elongated flexible band selectively circumscribing a person's body by at least partially covering abdomen region of the person;
a disc disposed on the elongated flexible band, the disc capable of securing the feeding tube; and
a sling mechanism capable of supporting the feeding tube, the sling mechanism comprising,
   a first structural element having a first end and a second end, the first structural element capable of securing a portion of the feeding tube, and
   a second structural element having a first end and a second end, the second structural element capable of supporting the first structural element;
wherein the first end of the first structural element is connected to the disc and the first end of the second structural element is connected to the elongated flexible band,
wherein the second end of the first structural element is not in contact with the first end of the second structural element, and
wherein the second end of the second structural element is in contact with the second end of the first structural element.

2. The support system of claim 1, further comprising cooperative fasteners disposed at opposite ends of the elongated flexible band along a length of the elongated flexible band, the cooperative fasteners configured to detachably secure the opposite ends of the elongated flexible band to circumscribe the person's body.

3. The support system of claim 2, wherein the cooperative fasteners are Velcro fasteners.

4. The support system of claim 1, wherein the disc is disposed at a central portion of the elongated flexible band.

5. The support system of claim 1, wherein the second end of the first structural element and the second end of the second structural element comprise a locking mechanism such that the second structural element is capable of supporting the first structural element.

6. A support system for a feeding tube, comprising:
an elongated flexible band adapted to circumscribe a person's body by at least partially covering abdomen region of the person;
a disc detachably disposed on the elongated flexible band, the disc capable of securing the feeding tube; and
a sling mechanism capable of supporting the feeding tube the sling mechanism comprising,
   a first structural element having a first end and a second end, the first structural element capable of securing a portion of the feeding tube, and
   a second structural element having a first end and a second end, the second structural element capable of supporting the first structural element;
wherein the first end of the first structural element is connected to the disc and the first end of the second structural element is connected to the elongated flexible band,
wherein the second end of the first structural element is not in contact with the first end of the second structural element, and
wherein the second end of the second structural element is in contact with the second end of the first structural element.

7. The support system of claim 6, further comprising cooperative fasteners disposed at opposite ends of the elongated flexible band along a length of the elongated flexible band, the cooperative fasteners configured to detachably secure the opposite ends of the elongated flexible band to circumscribe the person's body.

8. The support system of claim 7, wherein the cooperative fasteners are Velcro fasteners.

9. The support system of claim 6, wherein the disc comprises a pair of snap fasteners, the pair of snap fasteners capable of detachably coupling the disc with the elongated flexible band.

10. The support system of claim 6, wherein the disc is disposed at a central portion of the elongated flexible band.

11. The support system of claim 6, wherein the second end of the first structural element and the second end of the second structural element comprise a locking mechanism such that the second structural element is capable of supporting the first structural element.

* * * * *